(12) United States Patent
Jackson et al.

(10) Patent No.: US 9,415,620 B2
(45) Date of Patent: Aug. 16, 2016

(54) OPTICAL BRIGHTENING COMPOSITIONS FOR HIGH QUALITY INK JET PRINTING

(71) Applicant: CLARIANT FINANCE (BVI) LIMITED, Tortola (VG)

(72) Inventors: Andrew Clive Jackson, Muenchenstein BL (CH); Cedric Klein, Colmar (FR); David Puddiphatt, Grellingen BL (CH)

(73) Assignee: ARCHROMA IP GMBH, Reinach (CH)

( * ) Notice: Subject to any disclaimer, the term of this patent is extended or adjusted under 35 U.S.C. 154(b) by 0 days.

(21) Appl. No.: 14/635,144

(22) Filed: Mar. 2, 2015

(65) Prior Publication Data

US 2015/0197116 A1  Jul. 16, 2015

Related U.S. Application Data

(63) Continuation of application No. 13/131,425, filed as application No. PCT/EP2009/008258 on Nov. 20, 2009, now abandoned.

(30) Foreign Application Priority Data

Nov. 27, 2008 (EP) .................... 08170103
Nov. 27, 2008 (EP) .................... 08170132
Jul. 2, 2009 (EP) .................... 09164400

(51) Int. Cl.
| | | |
|---|---|---|
| C08K 5/34 | (2006.01) | |
| B41M 5/52 | (2006.01) | |
| D21H 21/30 | (2006.01) | |
| B41J 2/01 | (2006.01) | |
| C07D 251/54 | (2006.01) | |
| D21H 17/66 | (2006.01) | |
| D21H 21/16 | (2006.01) | |

(52) U.S. Cl.
CPC ............. B41M 5/5227 (2013.01); B41J 2/01 (2013.01); B41M 5/5236 (2013.01); B41M 5/5245 (2013.01); B41M 5/5254 (2013.01); C07D 251/54 (2013.01); D21H 21/30 (2013.01); *D21H 17/66* (2013.01); *D21H 21/16* (2013.01)

(58) Field of Classification Search
CPC ............ B41M 5/5227; B41M 5/5254; B41M 5/5236; B41M 5/5245; B41J 2/01; C07D 251/54
USPC ......................................................... 524/100
See application file for complete search history.

(56) References Cited

U.S. PATENT DOCUMENTS

| | | | |
|---|---|---|---|
| 3,728,275 A | 4/1973 | Horlacher et al. | |
| 6,207,258 B1 | 3/2001 | Varnell | |
| 2004/0111812 A1* | 6/2004 | Yamaguchi | C07D 251/68 8/648 |
| 2005/0022320 A1 | 2/2005 | Jackson | |
| 2006/0252872 A1 | 11/2006 | Jonckheree | |
| 2009/0081475 A1* | 3/2009 | Jackson | D21H 19/46 428/537.5 |
| 2010/0171384 A1 | 7/2010 | Elmaleh | |

FOREIGN PATENT DOCUMENTS

| | | |
|---|---|---|
| CN | 85101757 A | 1/1987 |
| CN | 1265625 A | 9/2000 |
| CN | 1795107 A | 6/2006 |
| CN | 101094842 A | 12/2007 |
| EP | 1612209 A1 | 1/2006 |
| EP | 1 612 209 A1 | 4/2006 |
| EP | 2 135 997 A1 | 12/2009 |
| JP | 2007503520 A | 2/2007 |
| JP | 2007536133 A | 12/2007 |
| JP | 2008534762 A | 8/2008 |
| TW | 1300065 B | 8/2008 |
| WO | 99/06219 A1 | 2/1999 |
| WO | 02055646 A1 | 7/2002 |
| WO | 02/060883 A1 | 8/2002 |
| WO | 2004/106079 A2 | 12/2004 |
| WO | 2005/105469 A1 | 11/2005 |
| WO | 2006/108785 A2 | 10/2006 |
| WO | 2006108785 A2 | 10/2006 |
| WO | 2007005368 A1 | 1/2007 |
| WO | 2007/053681 A1 | 5/2007 |
| WO | 2009/118247 A1 | 10/2009 |
| WO | 2009/145790 A1 | 12/2009 |
| WO | 2010/039996 A1 | 4/2010 |
| WO | 2010/068193 A1 | 6/2010 |

OTHER PUBLICATIONS

International Search Report for International Application No. PCT/EP2009/008258 mailed Feb. 4, 2010.
Opposition against EP 2370632 (09755848.0).
Opposition against EP 2370632 (09755848.0), Oct. 6, 2015.
Petition for the Imposition of Antidumping Duties, vol. I: Required Information, Material Injury, and Threat of Maerial Injury, Public Version, filed by Clariant Corporation, Dated Mar. 31, 2011, pp. 1-58 and Table of Exhibits.
Data sheet on Cartabond® Crosslinkers for improved offset printing and converting, Clariant, 2011 (from internet).
Extract of Handbook of Paper and Board, 2nd edition, Ed. Herbert Holik, 2013, pp. 214-226 (Wet-Strength Resins (WSA); Epoxidized Polyamide Resins, Other Wet-Strength Resins).

* cited by examiner

*Primary Examiner* — Hui Chin
(74) *Attorney, Agent, or Firm* — McBee Moore Woodward Vanik, IP, LLC

(57) ABSTRACT

The instant invention relates to improved liquid sizing compositions comprising derivatives of diaminostilbene, binders, protective polymers and divalent metal salts for the optical brightening of substrates suitable for high quality ink jet printing.

20 Claims, No Drawings

OPTICAL BRIGHTENING COMPOSITIONS FOR HIGH QUALITY INK JET PRINTING

This application is a continuation application of U.S. Ser. No. 13/131,425 (filed May 26, 2011) which is a 371 National Stage of PCT/EP2009/008258 (filed Nov. 20, 2009), which claims priority to EP 08170103.9 and EP 08170132.8 (both filed Nov. 8, 2008) and EP 09164400.5 (filed Jul. 2, 2009) the contents of all are incorporated herein by reference in their entirety.

The instant invention relates to improved liquid sizing compositions comprising derivatives of diaminostilbene, binders, protective polymers and divalent metal salts for the optical brightening of substrates suitable for high quality ink jet printing.

BACKGROUND OF THE INVENTION

Ink jet printing has in recent years become a very important means for recording data and images onto a paper sheet. Low costs, easy production of multicolor images and relatively high speed are some of the advantages of this technology. Ink jet printing does however place great demands on the substrate in order to meet the requirements of short drying time, high print density and sharpness, and reduced color-to-color bleed. Furthermore, the substrate should have a high brightness. Plain papers for example are poor at absorbing the water-based anionic dyes or pigments used in ink jet printing; the ink remains for a considerable time on the surface of the paper which allows diffusion of the ink to take place and leads to low print sharpness. One method of achieving a short drying time while providing high print density and sharpness is to use special silica-coated papers. Such papers however are expensive to produce.

U.S. Pat. No. 6,207,258 provides a partial solution to this problem by disclosing that pigmented ink jet print quality can be improved by treating the substrate surface with an aqueous sizing medium containing a divalent metal salt. Calcium chloride and magnesium chloride are preferred divalent metal salts. The sizing medium may also contain other conventional paper additives used in treating uncoated paper. Included in conventional paper additives are optical brightening agents (OBAs) which are well known to improve considerably the whiteness of paper and thereby the contrast between the ink jet print and the background. U.S. Pat. No. 6,207,258 offers no examples of the use of optical brightening agents with the invention.

WO 2007/044228 claims compositions including an alkenyl succinic anhydride sizing agent and/or an alkyl ketene dimmer sizing agent, and incorporating a metallic salt. No reference is made to the use of optical brightening agents with the invention.

WO 2008/048265 claims a recording sheet for printing comprising a substrate formed from ligno cellulosic fibers of which at least one surface is treated with a water soluble divalent metal salt. The recording sheet exhibits an enhanced image drying time. Optical brighteners are included in a list of optional components of a preferred surface treatment comprising calcium chloride and one or more starches. No examples are provided of the use of optical brighteners with the invention.

WO 2007/053681 describes a sizing composition that, when applied to an ink jet substrate, improves print density, color-to-color bleed, print sharpness and/or image dry time. The sizing composition comprises at least one pigment, preferably either precipitated or ground calcium carbonate, at least one binder, one example of which is a multicomponent system including starch and polyvinyl alcohol, at least one nitrogen containing organic species, preferably a polymer or copolymer of diallyldimethyl ammonium chloride (DADMAC), and at least one inorganic salt. The sizing composition may also contain at least one optical brightening agent.

The advantages of using a divalent metal salt, such as calcium chloride, in substrates intended for pigmented ink jet printing can only be fully realized when a compatible water-soluble optical brightener becomes available. It is well-known however that water-soluble optical brighteners are prone to precipitation in high calcium concentrations. (See, for example, page 50 in Tracing Technique in Geohydrology by Werner Käss and Horst Behrens, published by Taylor & Francis, 1998).

Accordingly, there is a need for improved optical brightening compositions which have good compatibility with sizing compositions containing a divalent metal salt.

DESCRIPTION OF THE INVENTION

It has now been found that certain polymers are surprisingly effective at improving the compatibility of optical brighteners of formula (1) with sizing compositions containing a divalent metal salt. Such polymers are henceforth referred to as protective polymers.

The present invention therefore provides a sizing composition for optical brightening of substrates, preferably paper, which is especially suitable for pigmented ink jet printing, comprising
(a) at least one optical brightener of formula (1);

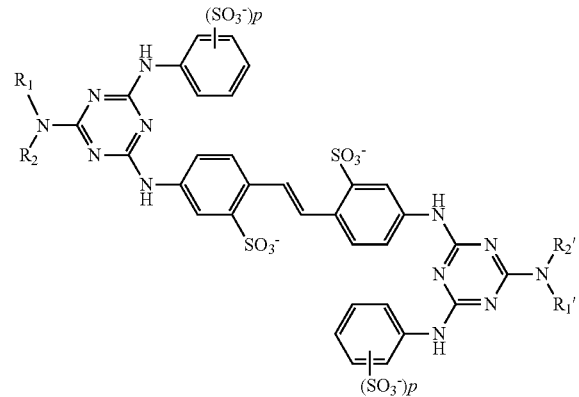

(1)

in which
the anionic charge on the brightener is balanced by a cationic charge composed of one or more identical or different cations selected from the group consisting of hydrogen, an alkali metal cation, alkaline earth metal, ammonium, ammonium which is mono-, di- or trisubstituted by a $C_1$-$C_4$ linear or branched alkyl radical, ammonium which is mono-, di- or trisubstituted by a $C_1$-$C_4$ linear or branched hydroxyalkyl radical, or mixtures of said compounds, $R_1$ and $R_1'$ may be the same or different, and each is hydrogen, $C_1$-$C_4$ linear or branched alkyl, $C_2$-$C_4$ linear or branched hydroxyalkyl, $CH_2CO_2^-$, $CH_2CH_2CONH_2$ or $CH_2CH_2CN$, $R_2$ and $R_2'$ may be the same or different, and each is $C_1$-$C_4$ linear or branched alkyl, $C_2$-$C_4$ linear or branched hydroxyalkyl, $CH_2CO_2^-$, $CH(CO_2^-)CH_2CO_2^-$, $CH(CO_2^-)CH_2CH_2CO_2^-$, $CH_2CH_2SO_3^-$, benzyl, or $R_1$ and $R_2$ and/or $R_1'$ and $R_2'$, together with the neighboring nitrogen atom signify a morpholine ring and p is 0, 1 or 2;

(b) at least one binder, the binder being selected from the group consisting of native starch, enzymatically modified starch and chemically modified starch;

(c) at least one divalent metal salt, the divalent metal salts being selected from the group consisting of calcium chloride, magnesium chloride, calcium bromide, magnesium bromide, calcium iodide, magnesium iodide, calcium nitrate, magnesium nitrate, calcium formate, magnesium formate, calcium acetate, magnesium acetate, calcium citrate, magnesium citrate, calcium gluconate, magnesium gluconate, calcium ascorbate, magnesium ascorbate, calcium sulfite, magnesium sulfite, calcium bisulfite, magnesium bisulfite, calcium dithionite, magnesium dithionite, calcium sulphate, magnesium sulphate, calcium thiosulphate, magnesium thiosulphate and mixtures of said compounds;

(d) at least one protective polymer which can be:

(i) a polyethylene glycol;

(ii) a polyvinyl alcohol or a carboxylic acid containing polyvinyl alcohol;

(iii) a homopolymer of methacrylic acid;

(iv) a copolymer of acrylic acid or methacrylic acid with acrylamide or methacrylamide;

(v) a cationic copolymer of acrylamide or methacrylamide with diallyldimethylammonium chloride;

(vi) a polycationic polyquaternary product obtainable by reaction of an oligohydroxyalkane of the formula $$X-(OH)_{x1} \quad \quad (Ia),$$

in which

X is the x1-valent radical of a $C_{3-6}$-alkane, and x1 is a number from 3 to the number of carbon atoms in X, or a mixture of oligohydroxyalkanes of formula (Ia), or a mixture of one or more oligohydroxyalkanes of formula (Ia) with a $C_{2-3}$-alkanediol, with epichlorohydrin, in the ratio of (2 to 2-x1) moles of epichlorohydrin for every mole of oligohydroxy-$C_{3-6}$-alkane of formula (Ia) plus 1-4 moles of epichlorohydrin for every molequivalent of $C_{2-3}$-alkanediol, to give a chloroterminated adduct ($E_1$), and reaction of ($E_1$) by cross-linking, quaternizing reaction with at least one aminocompound of formula

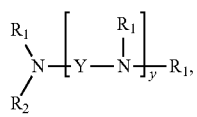

(II)

in which

Y is $C_{2-3}$-alkylene, y is a number from 0 to 3, $R_1$ is $C_{1-3}$-alkyl or $C_{2-3}$-hydroxyalkyl, and $R_2$ is $C_{1-3}$-alkyl or $C_{2-3}$-hydroxyalkyl, if y is 1 to 4, or hydrogen, if y is 0;

(e) water.

Optionally a chain-terminating, quaternizing reaction with a tertiary amine of the formula $N(R_1)_3$ may follow in the production of the polycationic polyquaternary product (vi).

In optical brighteners for which p is 1, the $SO_3^-$ group is preferably in the 4-position of the phenyl group.

In optical brighteners for which p is 2, the $SO_3^-$ groups are preferably in the 2,5-positions of the phenyl group.

The polycationic polymer (vi) is described in WO 99/67463 in more detail.

Preferred compounds of formula (1) are those in which the anionic charge on the brightener is balanced by a cationic charge composed of one or more identical or different cations selected from the group consisting of hydrogen, an alkali metal cation, alkaline earth metal, ammonium which is mono-, di- or trisubstituted by a $C_1$-$C_4$ linear or branched hydroxyalkyl radical, or mixtures of said compounds, $R_1$ and $R_1'$ may be the same or different, and each is hydrogen, $C_1$-$C_4$ linear or branched alkyl, $C_2$-$C_4$ linear or branched hydroxyalkyl, $CH_2CO_2^-$, $CH_2CH_2CONH_2$ or $CH_2CH_2CN$, $R_2$ and $R_2'$ may be the same or different, and each is $C_1$-$C_4$ linear or branched alkyl, $C_2$-$C_4$ linear or branched hydroxyalkyl, $CH_2CO_2^-$, $CH(CO_2^-)CH_2CO_2^-$ or $CH(CO_2^-)CH_2CH_2CO_2^-$ and p is 0, 1 or 2.

More preferred compounds of formula (1) are those in which the anionic charge on the brightener is balanced by a cationic charge composed of one or more identical or different cations selected from the group consisting of Li, Na, K, Ca, Mg, ammonium which is mono-, di- or trisubstituted by a $C_1$-$C_4$ linear or branched hydroxyalkyl radical, or mixtures of said compounds, $R_1$ and $R_1'$ may be the same or different, and each is hydrogen, methyl, ethyl, α-methylpropyl, β-methylpropyl, β-hydroxyethyl, β-hydroxypropyl, $CH_2CO_2^-$, $CH_2CH_2CONH_2$ or $CH_2CH_2CN$, $R_2$ and $R_2'$ may be the same or different, and each is methyl, ethyl, α-methylpropyl, β-methylpropyl, β-hydroxyethyl, β-hydroxypropyl, $CH_2CO_2^-$ or $CH(CO_2^-)CH_2CO_2^-$, and p is 0, 1 or 2.

Especially preferred compounds of formula (1) are those in which the anionic charge on the brightener is balanced by a cationic charge composed of one or more identical or different cations selected from the group consisting of Na, K and triethanolamine or mixtures of said compounds, $R_1$ and $R_1'$ may be the same or different, and each is hydrogen, ethyl, β-hydroxyethyl, β-hydroxypropyl, $CH_2CO_2^-$, or $CH_2CH_2CN$, $R_2$ and $R_2'$ may be the same or different, and each is ethyl, 3-hydroxyethyl, β-hydroxypropyl, $CH_2CO_2^-$ or $CH(CO_2^-)CH_2CO_2^-$, and p is 2.

The concentration of optical brightener in the sizing composition may be between 0.2 and 30 g/l, preferably between 1 and 25 g/l, most preferably between 2 and 20 g/l.

The binder is selected from the group consisting of native starch, enzymatically modified starch and chemically modified starch. Modified starches are preferably oxidized starch, hydroxyethylated starch or acetylated starch. The native starch is preferably an anionic starch, an cationic starch, or an amphoteric starch. While the starch source may be any, preferably the starch sources are corn, wheat, potato, rice, tapioca or sago.

The concentration of binder in the sizing composition may be between 1 and 30% by weight, preferably between 2 and 20% by weight, most preferably between 5 and 15% by weight.

More preferred divalent metal salts are selected from the group consisting of calcium chloride, magnesium chloride, calcium bromide, magnesium bromide, calcium sulphate, magnesium sulphate, calcium thiosulphate or magnesium thiosulphate or mixtures of said compounds.

Especially preferred divalent metal salts are selected from the group consisting of calcium chloride or magnesium chloride or mixtures of said compounds.

The concentration of divalent metal salt in the sizing composition may be between 1 and 100 g/l, preferably between 2 and 75 g/l, most preferably between 5 and 50 g/l.

When the divalent metal salt is a mixture of one or more calcium salts and one or more magnesium salts, the amount of calcium salts may be in the range of 0.1 to 99.9%.

The polyethylene glycol which may be employed as component (d) has an average molecular weight in the range of 100 to 8000, preferably in the range of 200 to 6000, most preferably in the range of 300 to 4500. When used as component (d), the weight ratio of polyethylene glycol to component (a) may be between 0.04:1 and 5:1, preferably between 0.05:1 and 2:1, most preferably between 0.1:1 and 1:1.

The polyvinyl alcohol which may be employed as component (d) has a degree of hydrolysis greater than or equal to 60% and a Brookfield viscosity of between 2 and 40 mPa·s for a 4% aqueous solution at 20° C. Preferably the degree of hydrolysis is between 70% and 95%, and the Brookfield viscosity is between 2 and 20 mPa·s (4% aqueous solution at 20° C.). Most preferably, the degree of hydrolysis is between 80% and 90%, and the Brookfield viscosity is between 2 and 20 mPa·s (4% aqueous solution at 20° C.). When used as component (d), the weight ratio of polyvinyl alcohol to component (a) may be between 0.01:1 and 2:1, preferably between 0.02:1 and 1:1, most preferably between 0.03:1 and 0.5:1.

The carboxylic acid containing polyvinyl alcohol which may be employed as component (d) has a degree of hydrolysis greater than or equal to 60% and a Brookfield viscosity of between 2 and 40 mPa·s for a 4% aqueous solution at 20° C. Preferably the degree of hydrolysis is between 70% and 95%, and the Brookfield viscosity is between 2 and 35 mPa·s (4% aqueous solution at 20° C.). Most preferably, the degree of hydrolysis is between 70% and 90%, and the Brookfield viscosity is between 2 and 30 mPa·s (4% aqueous solution at 20° C.). When used as component (d), the weight ratio of carboxylic acid containing polyvinyl alcohol to component (a) may be between 0.01:1 and 2:1, preferably between, 0.02:1 and 1:1, most preferably between 0.03:1 and 0.5:1.

The polymer of methacrylic acid which may be employed as component (d) has a Brookfield viscosity of between 100 and 40000 mPa·s for a 7-8% aqueous solution at 20° C. The polymer can be optionally used in its partial or full salt form. The preferred salt is Na, K, Ca, Mg, ammonium or ammonium which is mono-, di- or tri-substituted by a linear or branched alkyl or hydroxyalkyl radical. Preferably the viscosity is between 1000 and 30000 mPa·s (7-8% aqueous solution at 20° C.). Most preferably, the viscosity is between 5000 and 20000 mPa·s (7-8% aqueous solution at 20° C.). When used as component (d), the weight ratio of the polymer of methacrylic acid to component (a) may be between 0.0001:1 and 2:1, preferably between 0.001:1 and 1:1, most preferably between 0.002:1 and 0.5:1.

The copolymer of acrylic acid and acrylamide which may be employed as component (d) has a Brookfield viscosity of between 1 and 100 mPa·s for a 0.1% aqueous solution at 20° C. The copolymer can be either a block or a cross-linked copolymer. The copolymer can be optionally used in its partial or full salt form. The preferred salt is Na, K, Ca, Mg, ammonium or ammonium which is mono-, di- or tri-substituted by a linear or branched alkyl or hydroxyalkyl radical. Preferably the viscosity is between 1 and 80 mPa·s (0.1% aqueous solution at 20° C.). Most preferably, the viscosity is between 1 and 50 mPa·s (0.1% aqueous solution at 20° C.). When used as component (d), the weight ratio of the copolymer of acrylic or methacrylic acid and acrylamide or methacrylamide to component (a) may be between 0.001:1 and 1:1, preferably between 0.002:1 and 0.8:1, most preferably between 0.005:1 and 0.5:1.

The copolymer of methacrylic acid and methacrylamide which may be employed as component (d) has a Brookfield viscosity of between 1 and 100000 mPa·s for a 8% aqueous solution at 20° C. The copolymer can be either a block or a cross-linked copolymer. The copolymer can be optionally used in its partial or full salt form. The preferred salt is Na, K, Ca, Mg, ammonium or ammonium which is mono-, di- or tri-substituted by a linear or branched alkyl or hydroxyalkyl radical. Preferably the viscosity is between 10000 and 80000 mPa·s (8% aqueous solution at 20° C.). Most preferably, the viscosity is between 40000 and 50000 mPa·s (8% aqueous solution at 20° C.). When used as component (d), the weight ratio of the copolymer of methacrylic acid and methacrylamide to component (a) may be between 0.001:1 and 1:1, preferably between 0.002:1 and 0.8:1, most preferably between 0.005:1 and 0.5:1.

The cationic copolymer of an acrylamide or methacrylamide and diallyldimethylammonium chloride which may be employed as component (d) has a Brookfield viscosity of between 100 and 40000 mPa·s for a 10% aqueous solution at 20° C. The copolymer can be either a block or a cross-linked copolymer. Preferably the viscosity is between 500 and 30000 mPa·s 10% aqueous solution at 20° C.). Most preferably, the viscosity is between 9000 and 25000 mPa·s (10% aqueous solution at 20° C.). When used as component (d), the weight ratio of the cationic copolymer of acrylamide or methacrylamide and diallyldimethylammonium chloride to component (a) may be between 0.001:1 and 1:1, preferably between 0.005:1 and 0.8:1, most preferably between 0.01:1 and 0.5:1.

Other cationic polymers which may be employed as component (d) are fully described in WO 99/67463, especially those described in claim 4. The preparative process for the cationic polymer is characterized in that an oligohydroxyalkane is reacted with epichlorohydrin to give a chloro-terminated adduct which is then reacted with at least one aliphatic mono- or oligoamine to give a quaternized, optionally cross-linked, polymer. When used as component (d), the weight ratio of the cationic polymer to component (a) may be between 0.04:1 and 15:1, and preferably between 0.1:1 and 10:1.

The pH value of the sizing composition is typically in the range of 5-13, preferably 6-11.

In addition to one or more optical brighteners, one or more binders, one or more divalent metal salts, one or more protective polymers and water, the sizing composition may contain by-products formed during the preparation of the optical brightener as well as other conventional paper additives. Examples of such additives are antifreezes, biocides, defoamers, wax emulsions, dyes, inorganic salts, solubilizing aids, preservatives, complexing agents, thickeners, surface sizing agents, cross-linkers, pigments, special resins etc.

The sizing composition is prepared by adding the optical brightener, the protective polymer and the divalent metal salt to a preformed aqueous solution of the binder at a temperature of between 20° C. and 90° C.

In a preferred aspect of the invention the protective polymer is first formulated with an aqueous solution of the optical brightener. The protected brightener formulation is then added to an aqueous solution of the divalent metal salt and the binder at a temperature of between 50° C. and 70° C.

The sizing composition may be applied to the surface of a paper substrate by any surface treatment method known in the art. Examples of application methods include size-press applications, calendar size application, tub sizing, coating applications and spraying applications. (See, for example, pages 283-286 in Handbook for Pulp & Paper Technologists by G. A. Smook, $2^{nd}$ Edition Angus Wilde Publications, 1992 and US 2007/0277950.) The preferred method of application is at the size-press such as puddle size press. A preformed sheet of paper is passed through a two-roll nip which is flooded with the sizing composition. The paper absorbs some of the composition, the remainder being removed in the nip.

The paper substrate contains a web of cellulose fibres which may be sourced from any fibrous plant. Preferably the cellulose fibres are sourced from hardwood and/or softwood. The fibres may be either virgin fibres or recycled fibres, or any combination of virgin and recycled fibres.

The cellulose fibres contained in the paper substrate may be modified by physical and/or chemical methods as described, for example, in Chapters 13 and 15 respectively in Handbook for Pulp & Paper Technologists by G. A. Smook, $2^{nd}$ Edition Angus Wilde Publications, 1992. One example of a chemical modification of the cellulose fibre is the addition of an optical brightener as described, for example, in EP 0,884,312, EP 0,899,373, WO 02/055646, WO 2006/061399 and WO 2007/017336.

One example of an especially preferred optical brightener of formula (1) is described by formula (2). The preparation of a compound of formula (2) in which the anionic charge on the brightener is balanced by a cationic charge composed of 6 identical sodium cations has been described previously in WO 02/060883 and WO 02/077106. No examples have been provided of the preparation of a compound of formula (2) in which the anionic charge on the brightener is balanced by a cationic charge composed of a mixture of two or more different cations. The instant invention therefore also provides a method for the preparation of compounds of formula (2) in which the anionic charge on the brightener is balanced by a cationic charge composed of a mixture of two or more different cations, characterized in that different inorganic or organic bases are used simultaneously or separately from each other, either during or after the three stages of the reaction.

The compounds of formula (2) in which the anionic charge on the brightener is balanced by a cationic charge composed of a mixture of two or more different cations are therefore prepared by stepwise reaction of a cyanuric halide with
a) an amine of formula

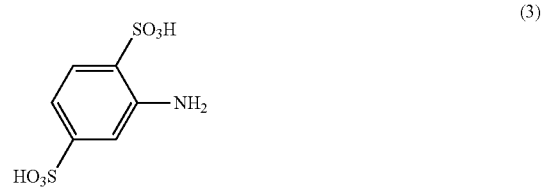 [SMILES: Nc1cc(S(=O)(=O)O)ccc1S(=O)(=O)O]

(3)

in the free acid, partial- or full salt form,
(b) a diamine of formula

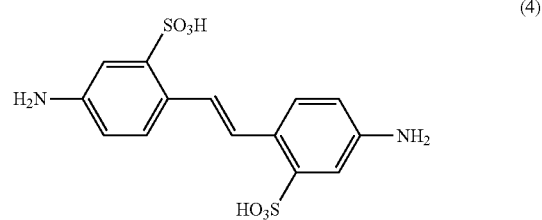 [SMILES: Nc1ccc(/C=C/c2ccc(N)cc2S(=O)(=O)O)c(S(=O)(=O)O)c1]

(4)

in the free acid, partial- or full salt form, and
c) diisopropanolamine of formula

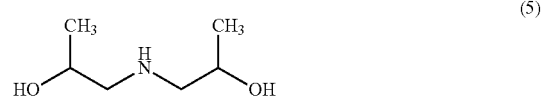

(5)

As a cyanuric halide there may be employed the fluoride, chloride or bromide. Cyanuric chloride is preferred.

Each reaction may be carried out in an aqueous medium, the cyanuric halide being suspended in water, or in an aque-

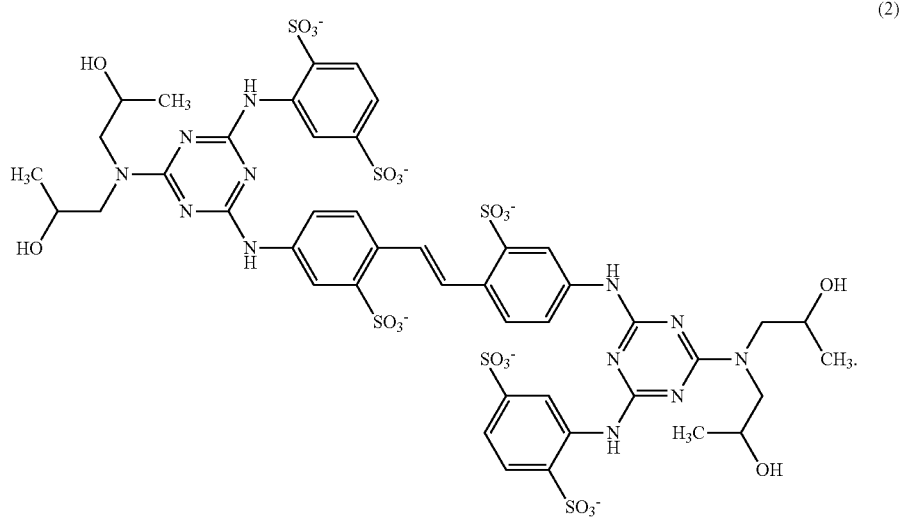

(2)

ous/organic medium, the cyanuric halide being dissolved in a solvent such as acetone. Each amine may be introduced without dilution, or in the form of an aqueous solution or suspension. The amines can be reacted in any order, although it is preferred to react the aromatic amines first. Each amine may be reacted stoichiometrically, or in excess. Typically, the aromatic amines are reacted stoichiometrically, or in slight excess; diisopropanolamine is generally employed in an excess of 5-30% over stoichiometry.

For substitution of the first halogen of the cyanuric halide, it is preferred to operate at a temperature in the range of 0 to 20° C., and under acidic to neutral pH conditions, preferably in the pH range of 2 to 7. For substitution of the second halogen of the cyanuric halide, it is preferred to operate at a temperature in the range of 20 to 60° C., and under weakly acidic to weakly alkaline conditions, preferably at a pH in the range of 4 to 8. For substitution of the third halogen of the cyanuric halide, it is preferred to operate at a temperature in the range of 60 to 102° C., and under weakly acidic to alkaline conditions, preferably at a pH in the range of 7 to 10.

The pH of each reaction is generally controlled by addition of a suitable base, the choice of base being dictated by the desired product composition. Preferred bases are, for example, alkali or alkaline earth metal (e.g., lithium, sodium, potassium, calcium, magnesium) hydroxides, carbonates or bicarbonates, or aliphatic tertiary amines e.g. triethanolamine or triisopropanolamine. Where a combination of two or more different bases is used, the bases may be added in any order, or at the same time.

Where it is necessary to adjust the reaction pH using acid, examples of acids that may be used include hydrochloric acid, sulphuric acid, formic acid and acetic acid.

Aqueous solutions containing one or more compounds of general formula (1) may optionally be desalinated either by membrane filtration or by a sequence of precipitation followed by solution using an appropriate base.

The preferred membrane filtration process is that of ultrafiltration using, e.g., polysulphone, polyvinylidenefluoride, cellulose acetate or thin-film membranes.

EXAMPLES

The following examples shall demonstrate the instant invention in more details. If not indicated otherwise, "parts" means "parts by weight" and "%" means "% by weight".

Preparative Example 1

Stage 1: 31.4 parts of aniline-2,5-disulphonic acid monosodium salt are added to 150 parts of water and dissolved with the aid of an approx. 30% sodium hydroxide solution at approx. 25° C. and a pH value of approx. 8-9. The obtained solution is added over a period of approx. 30 minutes to 18.8 parts of cyanuric chloride dispersed in 30 parts of water, 70 parts of ice and 0.1 part of an antifoaming agent. The temperature is kept below 5° C. using an ice/water bath and if necessary by adding ice into the reaction mixture. The pH is maintained at approx. 4-5 using an approx. 20% sodium carbonate solution. At the end of the addition, the pH is increased to approx. 6 using an approx. 20% sodium carbonate solution and stirring is continued at approx. 0-5° C. until completion of the reaction (3-4 hours).

Stage 2: 8.8 parts of sodium bicarbonate are added to the reaction mixture. An aqueous solution, obtained by dissolving under nitrogen 18.5 parts of 4,4'-diaminostilbene-2,2'-disulphonic acid in 80 parts of water with the aid of an approx. 30% sodium hydroxide solution at approx. 45-50° C. and a pH value of approx. 8-9, is dropped into the reaction mixture. The resulting mixture is heated at approx. 45-50° C. until completion of the reaction (3-4 hours).

Stage 3: 17.7 parts of Diisopropanolamine are then added and the temperature is gradually raised to approx. 85-90° C. and maintained at this temperature until completion of the reaction (2-3 hours) while keeping the pH at approx. 8-9 using an approx. 30% potassium hydroxide solution. The temperature is then decreased to 50° C. and the reaction mixture is filtered and cooled down to room temperature. The solution is adjusted to strength to give an aqueous solution of a compound of formula (2) in which the anionic charge on the brightener is balanced by a cationic charge composed of a mixture of sodium and potassium cations, the sodium cation being in the range 4.5-5.5 and the potassium cation being in the range 0.5-1.5 (0.125 mol/kg, approx. 18.0%).

Preparative Example 2

An aqueous solution of a compound of formula (2) in which the anionic charge on the brightener is balanced by a cationic charge composed of a mixture of sodium and potassium cations, the sodium cation being in the range 0-2.5 and the potassium cation being in the range 3.5-6 (0.125 mol/kg, approx. 18.8%) is obtained following the same procedure as in Example 1 with the sole differences that an approx. 30% potassium hydroxide and an approx. 20% potassium carbonate solutions are used instead of an approx. 30% sodium hydroxide and an approx. 20% sodium carbonate solutions in Stages 1 and 2, and 10 parts of potassium bicarbonate are used instead of 8.8 parts of sodium bicarbonate in Stage 2.

Preparative Example 1a

Optical brightening solution 1a is produced by stirring together
  an aqueous solution containing a compound of formula (2) prepared according to preparative example 1,
  a polyvinyl alcohol having a degree of hydrolysis of 85% and a Brookfield viscosity of 3.4-4.0 mPa·s, and
  water,
while heating to 90-95° C., until a clear solution is obtained that remains stable after cooling to room temperature.

The parts of each component are selected in order to get a final aqueous solution 1a comprising a compound of formula (2) prepared according to preparative example 1 at a concentration of 0.125 mol/kg and 2.5% of a polyvinyl alcohol having a degree of hydrolysis of 85% and a Brookfield viscosity of 3.4-4.0 mPa·s. The pH of solution 1a is in the range 8-9.

Preparative Example 1b

Optical brightening solution 1b is produced by stirring together
  an aqueous solution containing a compound of formula (2) prepared according to preparative example 1,
  a polyethylene glycol having an average molecular weight of 1500, and
  water,
while heating to 90-95° C., until a clear solution is obtained that remains stable after cooling to room temperature.

The parts of each component are selected in order to get a final aqueous solution 1b comprising a compound of formula (2) prepared according to preparative example 1 at a concentration of 0.125 mol/kg and 5% of a polyethylene glycol having an average molecular weight of 1500. The pH of solution 1b is in the range 8-9.

Preparative Example 2a

Optical brightening solution 2a is produced by stirring together
an aqueous solution containing compound of formula (2) prepared according to preparative example 2,
a polyvinyl alcohol having a degree of hydrolysis of 85% and a Brookfield viscosity of 3.4-4.0 mPa·s, and
water,
while heating to 90-95° C., until a clear solution is obtained that remains stable after cooling to room temperature.

The parts of each component are selected in order to get a final aqueous solution 2a comprising a compound of formula (2) prepared according to preparative example 2 at a concentration of 0.125 mol/kg and 2.5% of a polyvinyl alcohol having a degree of hydrolysis of 85% and a Brookfield viscosity of 3.4-4.0 mPa·s. The pH of solution 2a is in the range 8-9.

Preparative Example 2b

Optical brightening solution 2b is produced by stirring together
an aqueous solution containing a compound of formula (2) prepared according to preparative example 2,
a polyethylene glycol having an average molecular weight of 1500, and
water,
while heating to 90-95° C., until a clear solution is obtained that remains stable after cooling to room temperature.

The parts of each component are selected in order to get a final aqueous solution 2b comprising a compound of formula (2) prepared according to preparative example 2 at a concentration of 0.125 mol/kg and 5% of a polyethylene glycol having an average molecular weight of 1500. The pH of solution 2b is in the range 8-9.

Preparative Example 2c

Optical brightening solution 2c is produced by stirring together
an aqueous solution containing a compound of formula (2) prepared according to preparative example 2,
a carboxylic acid containing polyvinyl alcohol having a degree of hydrolysis between 85% and 90% and a Brookfield viscosity between 20 and 30 mPa·s for a 4% aqueous solution at 20° C., and
water,
while heating to 90-95° C., until a clear solution is obtained that remains stable after cooling to room temperature.

The parts of each component are selected in order to get a final aqueous solution 2c comprising a compound of formula (2) prepared according to preparative example 2 at a concentration of 0.125 mol/kg and 2.5% of a carboxylic acid containing polyvinyl alcohol having a degree of hydrolysis between 85% and 90% and a Brookfield viscosity between 20 and 30 mPa·s for a 4% aqueous solution at 20° C. The pH of solution 2c is in the range 8-9.

Preparative Example 2d

Optical brightening solution 2d is produced by stirring together
an aqueous solution containing a compound of formula (2) prepared according to preparative example 2,
a poly(acrylamide-co-acrylic acid) having a Brookfield viscosity between 2 and 3 mPa·s for a 0.1% aqueous solution at 20° C., and
water,
while heating to 90-95° C., until a clear solution is obtained that remains stable after cooling to room temperature.

The parts of each component are selected in order to get a final aqueous solution 2d comprising a compound of formula (2) prepared according to preparative example 2 at a concentration of 0.125 mol/kg and 0.5% of a poly(acrylamide-co-acrylic acid) having a Brookfield viscosity between 2 and 3 mPa·s for a 0.1 aqueous solution at 20° C. The pH of solution 2d is in the range 8-9.

Preparative Example 2e

Optical brightening solution 2e is produced by stirring together
an aqueous solution containing a compound of formula (2) prepared according to preparative example 2,
a 10 wt-% aqueous solution of poly(acrylamide-co-diallyldimethylammonium chloride) having a Brookfield viscosity between 9000 and 25000 mPa·s for a 10% aqueous solution at 20° C., and
water,
while heating to 90-95° C., until a clear solution is obtained that remains stable after cooling to room temperature.

The parts of each component are selected in order to get a final aqueous solution 2e comprising a compound of formula (2) prepared according to preparative example 2 at a concentration of 0.125 mol/kg and 10% of a 10 wt-% aqueous solution of poly(acrylamide-co-diallyldimethylammonium chloride) having a Brookfield viscosity between 9000 and 25000 mPa·s for a 10% aqueous solution at 20° C. The pH of solution 2e is in the range 8-9.

Preparative Example 3

Preparation of polymethacrylic acid ammonium salt polymer: 0.3 parts of radical initiator Vazo68 are mixed with 173 parts of methacrylic acid and 2000 parts of demineralized water. The mixture is stirred and heated under nitrogen to 74-76° C. over a period of 1 hour. After 10 minutes at 74-76° C., stirring is stopped and the mixture is left 16 hours at 74-76° C. 300 parts of demineralized water are added and the temperature is allowed to fall to 35° C. 178 parts of ammonia liquor are then slowly added and the resulting mixture is held at 35-40° C. for 6 hours. Stirring is re-started and maintained at 35-40° C. for 1 additional hour. The pH is then adjusted to approx. 9.0-11.0 by addition of ammonia liquor and the viscosity is adjust to 5000-20000 mPa·s by addition of water.

The aqueous solution so-formed (3000 parts) contains approx. 225 parts of polymethacrylic acid ammonium salt.

Preparative Example 3a

Optical brightening solution 3a is produced by stirring together
an aqueous solution containing compound of formula (2) prepared according to example 2,
an aqueous solution containing a polymethacrylic acid ammonium salt prepared according to preparative example 3 and having a viscosity of 5000-20000 mPa·s, and
water, while heating to 90-95° C., until a clear solution is obtained that remains stable after cooling to room temperature.

The parts of each component are selected in order to get a final aqueous solution 3a comprising a compound of formula (2) prepared according to preparative example 2 at a concentration of 0.125 mol/kg and 2.5% of an aqueous solution containing a polymethacrylic acid ammonium salt prepared according to preparative example 3 and having a viscosity of 5000-20000 mPa·s. The pH of solution 3a is in the range 8-9.

Preparative Example 4a

Optical brightening solution 4a is produced by stirring together
an aqueous solution containing a compound of formula (6),
a polyvinyl alcohol having a degree of hydrolysis of 85 W and a Brookfield viscosity of 3.4-4.0 mPa·s, and
water,
while heating to 90-95° C., until a clear solution is obtained that remains stable after cooling to room temperature.

The parts of each component are selected in order to get a final aqueous solution 4a comprising a compound of formula (6) at a concentration of 0.125 mol/kg and 2.5% of a polyvinyl alcohol having a degree of hydrolysis of 85% and a Brookfield viscosity of 3.4-4.0 mPa·s. The pH of solution 4a is in the range 8-9.

Preparative Example 5

Preparation of cationic polymer (Example 1 of WO 99/67463): 109.2 parts of sorbitol are mixed with 55.2 parts of glycerol and heated to 100° C. to form a solution. One part of boron trifluoride etherate is added, and the mixture is stirred and cooled to 70° C. 333 parts of epichlorohydrin are added dropwise over one hour at 70-80° C. with cooling. The reaction mixture is cooled to 20° C. and 135 parts of a 60% aqueous solution of diethylamine are added, and the reaction mixture is heated slowly to 90° C. and held there for one hour. The reaction mixture is then cooled to 50° C. and 150 parts of 30% sodium hydroxide and 100 parts of water are added. The mixture is held at 50-60° C. and the mixture slowly thickens as it polymerizes. During this time, extra water is added (275 parts) as the viscosity increases. Finally, when the reaction mixture reaches a viscosity of 1000 cP, the reaction is stopped by the addition of 20 parts of formic acid to give a pH of 4. The aqueous solution so-formed (1178 parts) contains 578 parts of cationic polymer.

Preparative Example 5a 300 parts of a solution of 55.5 parts of an optical brightener of formula (6) in water are gradually added at 50° C. to 700

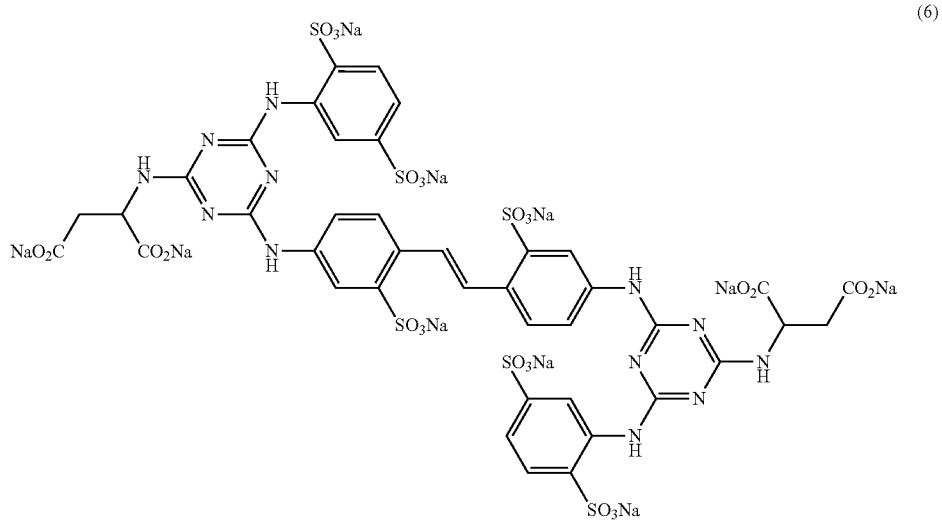

(6)

Preparative Example 4b

Optical brightening solution 4b is produced by stirring together
an aqueous solution containing a compound of formula (6),
a polyethylene glycol having an average molecular weight of 1500, and
water,
while heating to 90-95° C., until a clear solution is obtained that remains stable after cooling to room temperature.

The parts of each component are selected in order to get a final aqueous solution 4b comprising a compound of formula (6) at a concentration of 0.125 mol/kg and 5% of a polyethylene glycol having an average molecular weight of 1500. The pH of solution 4b is in the range 8-9.

parts of a stirred solution containing 343 parts of cationic polymer prepared according to preparative example 5. The solution so-formed contains 5.55% optical brightener (0.037 mol/kg) and 34.3% cationic polymer.

Preparative Example 6a

Optical brightening solution 6a is produced by stirring together
an aqueous solution containing a compound of formula (7),
a polyethylene glycol having an average molecular weight of 1500, and
water,
while heating to 90-95° C., until a clear solution is obtained that remains stable after cooling to room temperature.

The parts of each component are selected in order to get a final aqueous solution 6a comprising a compound of formula (7) at a concentration of 0.178 mol/kg and 5% of a polyethylene glycol having an average molecular weight of 1500. The pH of solution 6a is in the range 8-9.

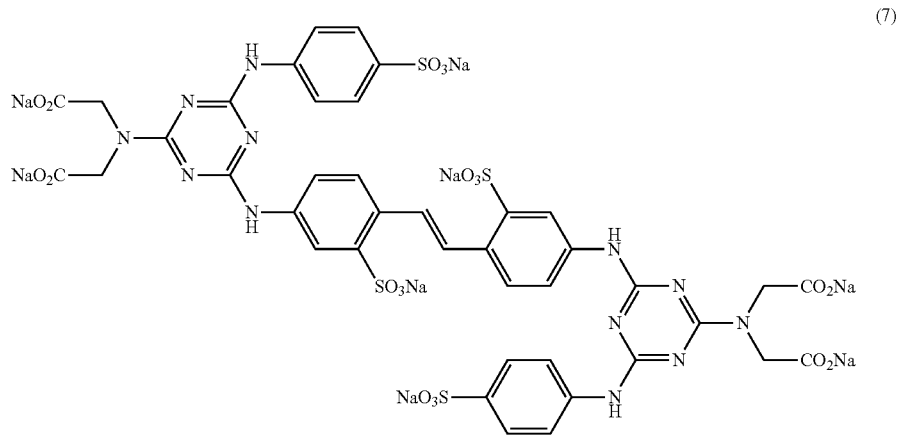

(7)

Preparative Example 7

Preparation of poly(methacrylamide-co-methacrylic acid): 0.15 parts of radical initiator Vazo68 are mixed with 43.25 parts of methacrylic acid, 43.18 parts of methacrylamide and 1000 parts of demineralized water. The mixture is stirred and heated under nitrogen to 74-76° C. over a period of 1 hour. After 10 minutes at 74-76° C., stirring is stopped and the mixture is left 16 hours at 74-76° C. 45.6 parts of aqueous sodium hydroxide (33%) are added, stirring is re-started and the temperature is allowed to fall to room temperature. The pH of the final product is approx. 7.0-8.0 and the viscosity is approx. 40000-50000 mPa·s.

The aqueous solution so-formed (1132 parts) contains approx. 90 parts of poly(methacrylamide-co-methacrylic acid) as its sodium salt.

Preparative Example 7a

Optical brightening solution 7a is produced by stirring together
  an aqueous solution containing a compound of formula (2) prepared according to preparative example 2,
  a poly(methacrylamide-co-methacrylic acid) prepared according to preparative example 7 and having a Brookfield viscosity between 40000 and 50000 mPa·s for a 8% aqueous solution at 20° C., and
  water,
while heating to 90-95° C., until a clear solution is obtained that remains stable after cooling to room temperature.

The parts of each component are selected in order to get a final aqueous solution 7a comprising a compound of formula (2) prepared according to preparative example 2 at a concentration of 0.125 mol/kg and 25% of a poly(methacrylamide-co-methacrylic acid) solution prepared according to preparative example 7 and having a Brookfield viscosity between 40000 and 50000 mPa·s for a 8% aqueous solution at 20° C. The pH of solution 7a is in the range 8-9.

Preparative Example 7b

Optical brightening solution 7b is produced by stirring together
  an aqueous solution containing a compound of formula (8),
  a poly(methacrylamide-co-methacrylic acid) prepared according to preparative example 7 and having a Brookfield viscosity between 40000 and 50000 mPa·s for a 8% aqueous solution at 20° C., and
  water,
while heating to 90-95° C., until a clear solution is obtained that remains stable after cooling to room temperature.

The parts of each component are selected in order to get a final aqueous solution 2d comprising a compound of formula (8) at a concentration of 0.125 mol/kg and 25% of a poly(methacrylamide-co-methacrylic acid) solution prepared according to preparative example 7 and having a Brookfield viscosity between 40000 and 50000 mPa·s for a 8% aqueous solution at 20° C. The pH of solution 7b is in the range 8-9.

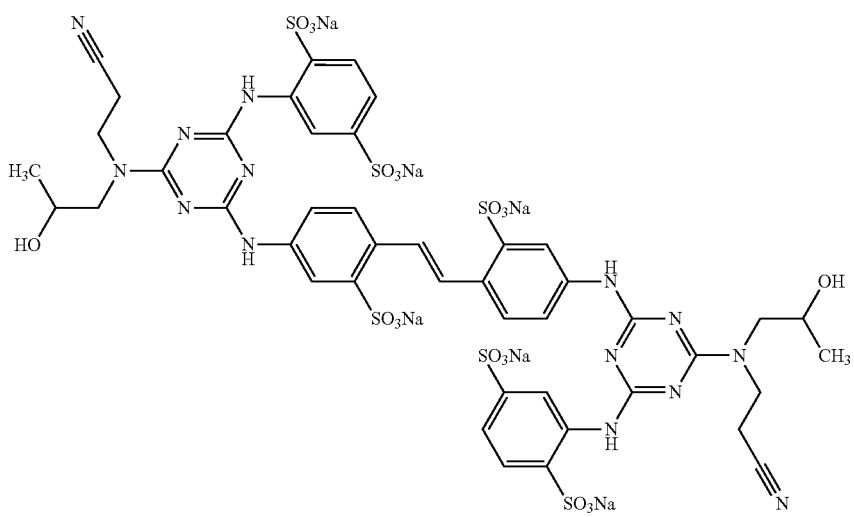

(8)

Preparative Example 7c

Optical brightening solution 7c is produced by stirring together
- an aqueous solution containing a compound of formula (8),
- a polyvinyl alcohol having a degree of hydrolysis of 85% and a Brookfield viscosity of 3.4-4.0 mPa·s, and
- water, while heating to 90-95° C., until a clear solution is obtained that remains stable after cooling to room temperature.

The parts of each component are selected in order to get a final aqueous solution 7c comprising a compound of formula (8) at a concentration of 0.125 mol/kg and 2.5% of a polyvinyl alcohol having a degree of hydrolysis of 85% and a Brookfield viscosity of 3.4-4.0 mPa·s. The pH of solution 7c is in the range 8-9.

Preparative Example 7d

Optical brightening solution 7d is produced by stirring together
- an aqueous solution containing a compound of formula (8),
- a polyacrylamide-co-acrylic acid) having a Brookfield viscosity between 2 and 3 mPa·s for a 0.1% aqueous solution at 20° C., and
- water, while heating to 90-95° C., until a clear solution is obtained that remains stable after cooling to room temperature.

The parts of each component are selected in order to get a final aqueous solution 7d comprising a compound of formula (8) at a concentration of 0.125 mol/kg and 0.5% of a poly(acrylamide-co-acrylic acid) having a Brookfield viscosity between 2 and 3 mPa·s for a 0.1% aqueous solution at 20° C. The pH of solution 7d is in the range 8-9.

Preparative Example 8

An aqueous solution of a compound of formula (2) in which the anionic charge on the brightener is balanced by a cationic charge composed of only sodium cations (0.150 mol/kg, approx. 21.4%) is obtained following the same procedure as in preparative example 1 with the sole differences that an approx. 30% sodium hydroxide is used instead of an approx. 30% potassium hydroxide in Stage 3 and that a smaller amount of water is added at the end of stage 3. The pH of the aqueous optical brightening solution obtained following this procedure is in the range 8-9.

Preparative Example 8a

Optical brightening solution 8a is produced by stirring together
- an aqueous solution containing a compound of formula (2) prepared according to preparative example 8,
- a polyvinyl alcohol having a degree of hydrolysis of 85% and a Brookfield viscosity of 3.4-4.0 mPa·s, and
- water, while heating to 90-95° C., until a clear solution is obtained that remains stable after cooling to room temperature.

The parts of each component are selected in order to get a final aqueous solution 8a comprising a compound of formula (2) prepared according to preparative example 8 at a concentration of 0.125 mol/kg and 2.5% by weight (based on the total weight of the final aqueous optical brightening solution 8a) of a polyvinyl alcohol having a degree of hydrolysis of 85% and a Brookfield viscosity of 3.4-4.0 mPa·s. The pH of the final aqueous optical brightening solution 8a obtained following this procedure is in the range 8-9.

Comparative Example 1

Without Protective Polymer

Comparative optical brightening solution 1 containing compound of formula (2) in which the anionic charge on the brightener is balanced by a cationic charge composed of a mixture of sodium and potassium cations, the sodium cation being in the range 4.5-5.5 and the potassium cation being in the range 0.5-1.5 is prepared according to preparative example 1 at a concentration of 0.125 mol/kg and a pH in the range 8-9.

Comparative Example 2

Without Protective Polymer

Comparative optical brightening solution 2 containing a compound of formula (2) in which the anionic charge on the brightener is balanced by a cationic charge composed of a mixture of sodium and potassium cations, the sodium cation being in the range 0-2.5 and the potassium cation being in the range 3.5-6 is prepared according to preparative example 2 at a concentration of 0.125 mol/kg and a pH in the range 8-9.

Comparative Example 4

Without Protective Polymer

Comparative optical brightening solution 4 containing a compound of formula (6) is adjusted to a concentration of 0.125 mol/kg by addition of water.

Comparative Example 6

Without Protective Polymer

Comparative optical brightening solution 6 containing a compound of formula (7) is adjusted to a concentration of 0.178 mol/kg by addition of water.

Comparative Example 7

Without Protective Polymer

Comparative optical brightening solution 7 containing a compound of formula (8) is adjusted to a concentration of 0.125 mol/kg by addition of water.

Comparative Example 8b

Without Protective Polymer

Comparative optical brightening solution 8b containing compound of formula (2) in which the anionic charge on the brightener is balanced by a cationic charge composed of only sodium cations is prepared by adding the proper amount of water to the aqueous optical brightening solution prepared according to preparative example 8 at such a rate that the final concentration of compound of formula (2) in which the anionic charge on the brightener is balanced by a cationic charge composed of only sodium cations is 0.125 mol/kg. The pH of the final aqueous optical brightening solution 8b obtained following this procedure is in the range 8-9.

Application Examples 1a-b, 2a-e and 3a

Sizing compositions are prepared by adding an aqueous solution prepared according to preparative examples 1a-b, 2a-e and 3a at a range of concentrations from 0 to 80 g/l to a stirred, aqueous solution of calcium chloride (35 g/l) and an anionic starch (50 g/l) (Penford Starch 260) at 60° C. The sizing solution is allowed to cool, then poured between the moving rollers of a laboratory size-press and applied to a commercial 75 g/m$^2$ AKD (alkyl ketene dimer) sized, bleached paper base sheet. The treated paper is dried for 5 minutes at 70° C. in a flat bed drier. The dried paper is allowed to condition, and then measured for CIE whiteness on a calibrated Auto Elrepho spectrophotometer. The results are shown in Table 1.

Comparative Application Examples 1 and 2

Sizing compositions are prepared by adding an aqueous solution prepared according to comparative examples 1 and 2 at a range of concentrations from 0 to 80 g/l to a stirred, aqueous solution of calcium chloride (35 g/l) and an anionic starch (50 g/l) (Penford Starch 260) at 60° C. The sizing solution is allowed to cool, then poured between the moving rollers of a laboratory size-press and applied to a commercial 75 g/m$^2$ AKD (alkyl ketene dimer) sized, bleached paper base sheet. The treated paper is dried for 5 minutes at 70° C. in a flat bed drier.

The dried paper is allowed to condition, and then measured for CIE whiteness on a calibrated Auto Elrepho spectrophotometer. The results are shown in Table 1.

Application Examples 4a and 4b

Sizing compositions are prepared by adding an aqueous solution prepared according to preparative examples 4a and 4b at a range of concentrations from 0 to 80 g/l to a stirred, aqueous solution of calcium chloride (35 g/l) and an anionic starch (50 g/l) (Penford Starch 260) at 60° C. The sizing solution is allowed to cool, then poured between the moving rollers of a laboratory size-press and applied to a commercial 75 g/m$^2$ AKD (alkyl ketene dimer) sized, bleached paper base sheet. The treated paper is dried for 5 minutes at 70° C. in a flat bed drier.

The dried paper is allowed to condition, and then measured for CIE whiteness on a calibrated Auto Elrepho spectrophotometer. The results are shown in Table 2.

Comparative Application Example 4

Sizing compositions are prepared by adding an aqueous solution prepared according to comparative example 4 at a range of concentrations from 0 to 80 g/l to a stirred, aqueous solution of calcium chloride (35 g/l) and an anionic starch (50 g/l) (Penford Starch 260) at 60° C. The sizing solution is allowed to cool, then poured between the moving rollers of a laboratory size-press and applied to a commercial 75 g/m$^2$ AKD (alkyl ketene dimer) sized, bleached paper base sheet. The treated paper is dried for 5 minutes at 70° C. in a flat bed drier.

The dried paper is allowed to condition, and then measured for CIE whiteness on a calibrated Auto Elrepho spectrophotometer. The results are shown in Table 2.

Application Examples 5a

Sizing compositions are prepared by adding an aqueous solution prepared according to preparative example 5a at a range of concentrations from 0 to 270 g/l (0 to 0.01 mol/l optical brightener) into a stirred, aqueous solution of calcium chloride (35 g/l) and an anionic starch (50 g/l) (Perfectamyl A4692) at 60° C. The sizing solution is allowed to cool, then poured between the moving rollers of a laboratory size-press and applied to a commercial 75 g/m$^2$ AKD (alkyl ketene dimer) sized, bleached paper base sheet. The treated paper is dried for 5 minutes at 70° C. in a flat bed drier.

The dried paper is allowed to condition, and then measured for CIE whiteness on a calibrated Auto Elrepho spectrophotometer. The results are shown in Table 3.

Comparative Application Example 5

Sizing compositions are prepared by adding an aqueous solution prepared according to comparative example 4 at a range of concentrations from 0 to 80 g/l (0 to 0.01 mol/l optical brightener) into a stirred, aqueous solution of calcium chloride (35 g/l) and an anionic starch (50 g/l) (Perfectamyl A4692) at 60° C. The sizing solution is allowed to cod, then poured between the moving rollers of a laboratory size-press and applied to a commercial 75 g/m² AKD (alkyl ketene dimer) sized, bleached paper base sheet. The treated paper is dried for 5 minutes at 70° C. in a flat bed drier.

The dried paper is allowed to condition, and then measured for CIE whiteness on a calibrated Auto Elrepho spectrophotometer. The results are shown in Table 3.

Application Example 6a

Sizing compositions are prepared by adding an aqueous solution prepared according to preparative example 6a at a range of concentrations from 0 to 50 g/l to a stirred, aqueous solution of calcium chloride (8 g/l) and an anionic starch (50 g/l) (Perfectamyl A4692) at 60° C. The sizing solution is allowed to cool, then poured between the moving rollers of a laboratory size-press and applied to a commercial 75 g/m² AKD (alkyl ketene dimer) sized, bleached paper base sheet. The treated paper is dried for 5 minutes at 70° C. in a flat bed drier.

The dried paper is allowed to condition, and then measured for CIE whiteness on a calibrated Auto Elrepho spectrophotometer. The results are shown in Table 4.

Application Examples 6b

Sizing compositions are prepared by adding an aqueous solution prepared according to preparative example 6a at a range of concentrations from 0 to 50 g/l to a stirred, aqueous solution of magnesium chloride (8 g/l) and an anionic starch (50 g/l) (Perfectamyl A4692) at 60° C. The sizing solution is allowed to cool, then poured between the moving rollers of a laboratory size-press and applied to a commercial 75 g/m² AKD (alkyl ketene dimer) sized, bleached paper base sheet.

The treated paper is dried for 5 minutes at 70° C. in a flat bed drier.

The dried paper is allowed to condition, and then measured for CIE whiteness on a calibrated Auto Elrepho spectrophotometer. The results are shown in Table 4.

Comparative Application Example 6a'

Sizing compositions are prepared by adding an aqueous solution prepared according to comparative example 6 at a range of concentrations from 0 to 50 g/l to a stirred, aqueous solution of calcium chloride (8 g/l) and an anionic starch (50 g/l) (Perfectamyl A4692) at 60° C. The sizing solution is allowed to cool, then poured between the moving rollers of a laboratory size-press and applied to a commercial 75 g/m² AKD (alkyl ketene dimer) sized, bleached paper base sheet. The treated paper is dried for 5 minutes at 70° C. in a flat bed drier.

The dried paper is allowed to condition, and then measured for CIE whiteness on a calibrated Auto Elrepho spectrophotometer. The results are shown in Table 4.

Comparative Application Example 6b'

Sizing compositions are prepared by adding an aqueous solution prepared according to comparative example 6 at a range of concentrations from 0 to 50 g/l to a stirred, aqueous solution of magnesium chloride (8 g/l) and an anionic starch (50 g/l) (Perfectamyl A4692) at 60° C. The sizing solution is allowed to cool, then poured between the moving rollers of a laboratory size-press and applied to a commercial 75 g/m² AKD (alkyl ketene dimer) sized, bleached paper base sheet. The treated paper is dried for 5 minutes at 70° C. in a flat bed drier. The dried paper is allowed to condition, and then measured for CIE whiteness on a calibrated Auto Elrepho spectrophotometer. The results are shown in Table 4.

Application Example 7a

Sizing compositions are prepared by adding an aqueous solution prepared according to preparative example 7a at a range of concentrations from 0 to 80 g/l to a stirred, aqueous solution of calcium chloride (35 g/l) and an anionic starch (50 g/l) (Penford Starch 260) at 60° C. The sizing solution is allowed to cool, then poured between the moving rollers of a laboratory size-press and applied to a commercial 75 g/m² AKD (alkyl ketene dimer) sized, bleached paper base sheet. The treated paper is dried for 5 minutes at 70° C. in a flat bed drier. The dried paper is allowed to condition, and then measured for CIE whiteness on a calibrated Auto Elrepho spectrophotometer. The results are shown in Table 1.

Application Example 7b-d

Sizing compositions are prepared by adding an aqueous solution prepared according to preparative example 7b-d at a range of concentrations from 0 to 80 g/l to a stirred, aqueous solution of calcium chloride (35 g/l) and an anionic starch (50 g/l) (Penford Starch 260) at 60° C. The sizing solution is allowed to cool, then poured between the moving rollers of a laboratory size-press and applied to a commercial 75 g/m² AKD (alkyl ketene dimer) sized, bleached paper base sheet. The treated paper is dried for 5 minutes at 70° C. in a flat bed drier. The dried paper is allowed to condition, and then measured for CIE whiteness on a calibrated Auto Elrepho spectrophotometer. The results are shown in Table 5.

Comparative Application Example 7

Sizing compositions are prepared by adding an aqueous solution prepared according to comparative example 7 at a range of concentrations from 0 to 80 g/l to a stirred, aqueous solution of calcium chloride (35 g/l) and an anionic starch (50 g/l) (Penford Starch 260) at 60° C. The sizing solution is allowed to cool, then poured between the moving rollers of a laboratory size-press and applied to a commercial 75 g/m² AKD (alkyl ketene dimer) sized, bleached paper base sheet. The treated paper is dried for 5 minutes at 70° C. in a flat bed drier.

The dried paper is allowed to condition, and then measured for CIE whiteness on a calibrated Auto Elrepho spectrophotometer. The results are shown in Table 5.

Application Example 8a

Sizing compositions are prepared by adding an aqueous solution prepared according to preparative example 8a respectively at a range of concentrations from 0 to 80 g/l to a stirred, aqueous solution of calcium chloride (35 g/l) and an anionic starch (50 g/l) (Penford Starch 260) at 60° C. The sizing solution is allowed to cool, then poured between the moving rollers of a laboratory size-press and applied to a commercial 75 g/m² AKD (alkyl ketene dimer) sized, bleached paper base sheet. The treated paper is dried for 5 minutes at 70° C. in a flat bed drier. The dried paper is allowed to condition, and then measured for CIE whiteness on a calibrated Auto Elrepho spectrophotometer. The results are shown in Table 6.

Comparative Application Example 8b

Comparative sizing compositions are prepared by adding an aqueous solution prepared according to comparative example 8b respectively at a range of concentrations from 0 to 80 g/l to a stirred, aqueous solution of calcium chloride (35 g/l) and an anionic starch (50 g/l) (Penford Starch 260) at 60° C. The sizing solution is allowed to cool, then poured between the moving rollers of a laboratory size-press and applied to a commercial 75 g/m$^2$ AKD (alkyl ketene dimer) sized, bleached paper base sheet. The treated paper is dried for 5 minutes at 70° C. in a flat bed drier.

The dried paper is allowed to condition, and then measured for CIE whiteness on a calibrated Auto Elrepho spectrophotometer. The results are shown in Table 6.

The results in Tables 1, 2, 3, 4 and 5 and 6 clearly demonstrate the improved compatibility between the optical brightener and the divalent metal salt in the presence of the protective polymer.

TABLE 1

| OBA sol. conc. g/l | CIE Whiteness | | | | | | | | | Comparative application example | |
|---|---|---|---|---|---|---|---|---|---|---|---|
| | Application example | | | | | | | | | | |
| | 1a | 1b | 2a | 2b | 2c | 2d | 2e | 3a | 7a | 1 | 2 |
| 0 | 101.7 | 101.7 | 104.2 | 104.2 | 104.2 | 104.2 | 104.2 | 104.2 | 104.2 | 101.7 | 104.2 |
| 10 | 125.0 | 125.0 | 126.1 | 125.6 | 126.0 | 125.8 | 125.5 | 125.5 | 125.6 | 124.9 | 125.5 |
| 20 | 133.4 | 132.4 | 132.6 | 134.4 | 133.7 | 133.1 | 132.5 | 132.9 | 132.8 | 131.7 | 132.5 |
| 40 | 139.2 | 138.5 | 139.2 | 139.5 | 139.6 | 140.1 | 139.2 | 138.6 | 139.0 | 137.3 | 138.0 |
| 60 | 142.1 | 140.3 | 141.1 | 144.2 | 141.8 | 142.9 | 141.7 | 140.8 | 141.5 | 139.2 | 140.6 |
| 80 | 143.4 | 140.9 | 143.0 | 142.3 | 143.1 | 144.6 | 143.3 | 142.2 | 142.3 | 139.6 | 141.5 |

TABLE 2

| OBA sol. Conc. g/l | CIE Whiteness | | |
|---|---|---|---|
| | Application example | | Comparative application example |
| | 4a | 4b | 4 |
| 0 | 101.7 | 101.7 | 101.7 |
| 10 | 124.1 | 124.1 | 123.9 |
| 20 | 130.7 | 130.8 | 130.6 |
| 40 | 135.4 | 135.3 | 135.0 |
| 80 | 137.0 | 135.9 | 134.7 |

TABLE 3

| Concentration of optical brightener (mol/l) | CIE Whiteness | |
|---|---|---|
| | Application example 5a | Comparative application example 5 |
| 0 | 99.5 | 99.5 |
| 0.0025 | 124.0 | 123.6 |
| 0.0050 | 131.0 | 129.4 |
| 0.0075 | 136.6 | 131.6 |
| 0.0100 | 140.9 | 133.1 |

TABLE 4

| | CIE Whiteness | | | |
|---|---|---|---|---|
| | 8 g/l CaCl$_2$ | | 8 g/l MgCl$_2$ | |
| OBA sol. conc. g/l | Application example 6a | Comparative application example 6a' | Application example 6b | Comparative application example 6b' |
| 0 | 104.8 | 104.8 | 104.7 | 104.7 |
| 10 | 123.4 | 123.4 | 126.7 | 126.7 |
| 20 | 128.1 | 128.0 | 133.0 | 133.0 |
| 30 | 130.5 | 128.6 | 135.4 | 133.7 |
| 40 | 130.5 | 128.2 | 136.4 | 134.4 |
| 50 | 130.0 | 127.2 | 136.3 | 134.2 |

TABLE 5

| OBA sol. conc. g/l | CIE Whiteness | | | |
|---|---|---|---|---|
| | Application example | | | Comparative application example |
| | 7b | 7c | 7d | 7 |
| 0 | 103.3 | 103.3 | 103.3 | 103.3 |
| 10 | 124.1 | 123.2 | 122.4 | 122.8 |
| 20 | 131.3 | 131.1 | 132.1 | 131.0 |
| 40 | 135.9 | 135.8 | 137.7 | 135.8 |
| 60 | 137.7 | 137.2 | 139.4 | 136.0 |
| 80 | 136.7 | 136.03 | 141.0 | 135.4 |

TABLE 6

| OBA sol. conc. g/l | CIE Whiteness | |
|---|---|---|
| | Application example 8a | Comparative application example 8b |
| 0 | 104.4 | 104.4 |
| 10 | 125.2 | 124.3 |
| 20 | 132.1 | 131.3 |
| 40 | 138.7 | 137.7 |
| 60 | 141.9 | 140.5 |
| 80 | 143.6 | 141.3 |

The invention claimed is:

1. A sizing composition for optical brightening of a substrate for ink jet printing, comprising (a) at least one optical brightener of formula (1);

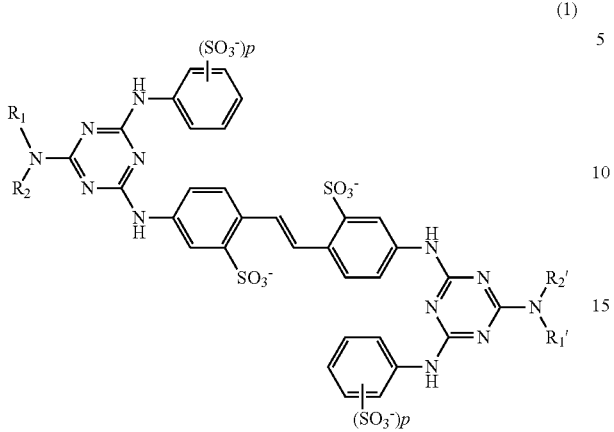

(1)

wherein,
the anionic charge on the at least one optical brightener is balanced by a cationic charge wherein the cationic charge is of one or more identical or different cations selected from the group consisting of hydrogen, an alkali metal cation, alkaline earth metal, ammonium, ammonium which is mono-, di- or trisubstituted by a $C_1$-$C_4$ linear or branched alkyl radical, ammonium which is mono-, di- or trisubstituted by a $C_1$-$C_4$ linear or branched hydroxyalkyl radical, and mixtures thereof,
$R_1$ and $R_1'$ are the same or different, and are hydrogen, $C_1$-$C_4$ linear or branched alkyl, $C_2$-$C_4$ linear or branched hydroxyalkyl, $CH_2CO_2^-$, $CH_2CH_2CONH_2$ or $CH_2CH_2CN$,
$R_2$ and $R_2'$ are the same or different, and are $C_1$-$C_4$ linear or branched alkyl, $C_2$-$C_4$ linear or branched hydroxyalkyl, $CH_2CO_2^-$, $CH(CO_2^-)CH_2CO_2^-$, $CH(CO_2^-)CH_2CH_2CO_2^-$, $CH_2CH_2SO_3^-$, benzyl, or
$R_1$ and $R_2$ together or $R_1'$ and $R_2'$, together or both form a morpholine ring with the neighbouring nitrogen, and
p is 0, 1 or 2;
(b) at least one binder selected from the group consisting of native starch, enzymatically modified starch and chemically modified starch;
(c) at least one divalent metal salt selected from the group consisting of calcium chloride, magnesium chloride, calcium bromide, magnesium bromide, calcium iodide, magnesium iodide, calcium nitrate, magnesium nitrate, calcium formate, magnesium formate, calcium acetate, magnesium acetate, calcium citrate, magnesium citrate, calcium gluconate, magnesium gluconate, calcium ascorbate, magnesium ascorbate, calcium sulfite, magnesium sulfite, calcium bisulfite, magnesium bisulfite, calcium dithionite, magnesium dithionite, calcium sulphate, magnesium sulphate, calcium thiosulphate and magnesium thiosulphate;
(d) at least one protective polymer selected from the group consisting of:
(i) a polyethylene glycol;
(ii) a polyvinyl alcohol or a carboxylic acid containing polyvinyl alcohol;
(iii) a homopolymer of methacrylic acid;
(iv) a copolymer of acrylic acid or methacrylic acid with acrylamide or methacrylamide;
(v) a cationic copolymer of acrylamide or methacrylamide with diallyldimethylammonium chloride; and
(vi) a polycationic polyquaternary product obtained by reacting an oligohydroxyalkane of the formula $$X-(OH)_{x1} \quad (Ia),$$

wherein
X is the x1-valent radical of a $C_{3-6}$-alkane, and
x1 is a number from 3 to the number of carbon atoms in X,
or a mixture of oligohydroxyalkanes of formula (Ia), and
or a mixture of one or more oligohydroxyalkanes of formula (Ia) with a $C_{2-3}$-alkanediol, with epichlorohydrin,
in the ratio of 2 to 2×1 moles of epichlorohydrin for every mole of oligohydroxy-$C_{3-6}$-alkane of formula (Ia) plus 1-4 moles of epichlorohydrin for every mole equivalent of $C_{2-3}$-alkanediol, to yield a chloro-terminated adduct ($E_1$), and reacting the chloro-terminated adduct ($E_1$) by a cross-linking, quaternizing reaction with at least one amino compound of formula

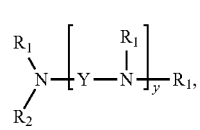

(II)

wherein
Y is $C_{2-3}$-alkylene,
y is a number from 0 to 3,
$R_1$ is $C_{1-3}$-alkyl or $C_{2-3}$-hydroxyalkyl, and
$R_2$ is $C_{1-3}$-alkyl or $C_{2-3}$-hydroxyalkyl, if y is 1 to 4, or hydrogen, if y is 0; and
(e) water.

2. The sizing composition according to claim 1 wherein the anionic charge on the at least one optical brightener is balanced by the cationic charge and wherein the cationic charge is identical or different cations selected from the group consisting of hydrogen, an alkali metal cation, alkaline earth metal, ammonium which is mono-, di- or trisubstituted by a $C_1$-$C_4$ linear or branched hydroxyalkyl radical, and mixtures therein, wherein
$R_1$ and $R_1'$ are the same or different, and hydrogen, $C_1$-$C_4$ linear or branched alkyl, $C_2$-$C_4$ linear or branched hydroxyalkyl, $CH_2CO_2^-$, $CH_2CH_2CONH_2$ or $CH_2CH_2CN$,
$R_2$ and $R_2'$ are the same or different, and $C_1$-$C_4$ linear or branched alkyl, $C_2$-$C_4$ linear or branched hydroxyalkyl, $CH_2CO_2^-$, $CH(CO_2^-)CH_2CO_2^-$ or $CH(CO_2^-)CH_2CH_2CO_2^-$, and
p is 0, 1 or 2.

3. The sizing composition according to claim 2 wherein the anionic charge on the brightener is balanced by a cationic charge and wherein the cationic charge is identical or different cations selected from the group consisting of Li, Na, K, Ca, Mg, ammonium which is mono-, di- or trisubstituted by a $C_1$-$C_4$ linear or branched hydroxyalkyl radical, and mixtures thereof,
wherein
$R_1$ and $R_1'$ are the same or different, and are hydrogen, methyl, ethyl, α-methylpropyl, β-methylpropyl, β-hydroxyethyl, β-hydroxypropyl, $CH_2CO_2^-$, $CH_2CH_2CONH_2$ or $CH_2CH_2CN$,
$R_2$ and $R_2'$ are the same or different, and are methyl, ethyl, α-methylpropyl, β-methylpropyl, β-hydroxyethyl, β-hydroxypropyl, $CH_2CO_2^-$ or $CH(CO_2^-)CH_2CO_2^-$,
p is 0, 1 or 2.

4. The sizing composition according to claim 3 wherein the anionic charge on the brightener is balanced by a cationic charge wherein the cationic charge is identical or different cations selected from the group consisting of Na, K, triethanolamine or mixtures thereof, wherein R$_1$ and R$_1$' are the same or different, and are hydrogen, ethyl, β-hydroxyethyl, β-hydroxypropyl, CH$_2$CO$_2$$^-$, or CH$_2$CH$_2$CN, R$_2$ and R$_2$' are the same or different, and are ethyl, β-hydroxyethyl, β-hydroxypropyl, CH$_2$CO$_2$$^-$ or CH(CO$_2$$^-$)CH$_2$CO$_2$$^-$ and p is 2.

5. The sizing composition according to claim 1, wherein the at least one divalent metal salt is calcium chloride, magnesium chloride or mixtures thereof.

6. The sizing composition according to claim 1, wherein the concentration of the at least one divalent metal salt is between 5 and 50 g/l.

7. The sizing composition according to claim 1, wherein the concentration of the at least one optical brightener is between 2 and 20 g/l.

8. The sizing composition according to claim 1, further comprising by-products formed during the preparation of the at least one optical brightener and at least one conventional paper additive selected from the group consisting of antifreezes, biocides, defoamers, wax emulsions, dyes, inorganic salts, solubilizing aids, preservatives, complexing agents, thickeners, surface sizing agents, cross-linkers, pigments and resins.

9. A process for preparing a sizing composition according to claim 1 comprising the step of adding the at least one optical brightener and the at least one divalent metal salt to a preformed aqueous solution of the at least one binder at a temperature of between 20° C. and 90° C.

10. An ink jet comprising a sizing composition according to claim 1 for optical brightening a substrate.

11. A process for preparing a brightened paper comprising the step of treating at least one surface of the paper with a sizing composition according to claim 1.

12. A process for the preparation of a compound of formula (2)

wherein the anionic charge is balanced by a cationic charge, wherein the cationic charge is a mixture of two or more different cations, comprising the step of reaction of a cyanuric halide, with a) an amine of formula

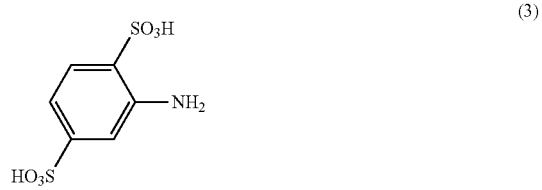

(3)

in the free acid, partial- or full salt form, (b) a diamine of formula

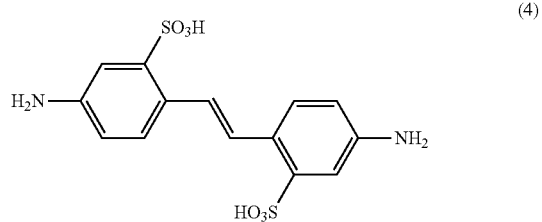 [SMILES: Nc1ccc(/C=C/c2ccc(N)cc2S(=O)(=O)O)c(S(=O)(=O)O)c1]

(4)

in the free acid, partial- or full salt form, and c) diisopropanolamine of formula

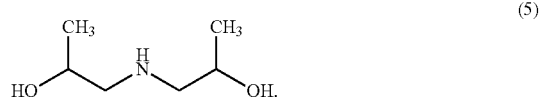

(5)

13. The process according to claim 12, wherein the substitution of the first halogen of the cyanuric halide is done at a temperature in the range of 0 to 20° C., and under acidic to (2)

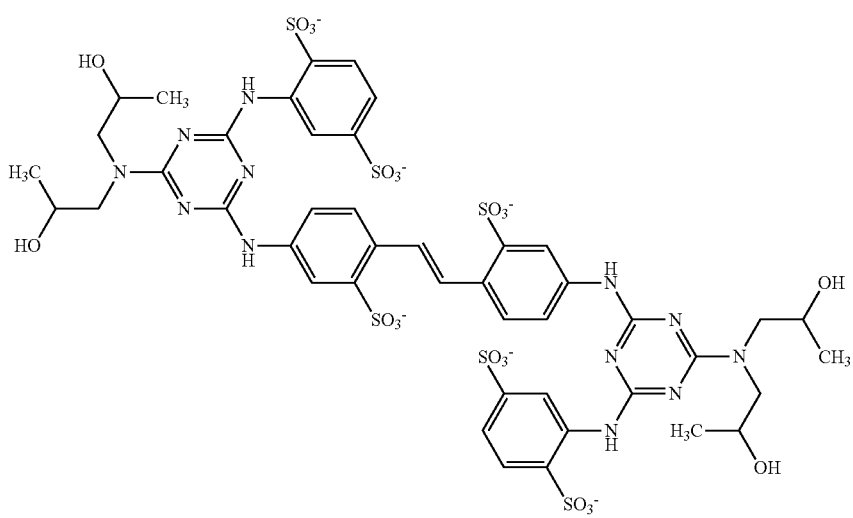

neutral pH conditions, the substitution of the second halogen of the cyanuric halide is done at a temperature in the range of 20 to 60° C., and under weakly acidic to weakly alkaline conditions and substitution of the third halogen of the cyanuric halide is done at a temperature in the range of 60 to 102° C., and under weakly acidic to alkaline conditions.

14. The ink jet as claimed in claim 10, wherein the substrate is paper.

15. The process as claimed in claim 11, wherein the treating step further comprises ink jet printing that at least one surface of the paper.

16. Brightened paper made in accordance with the process of claim 11.

17. The process as claimed in claim 12, wherein the cyanuric halide is cyanuric chloride.

18. The process according to claim 12, wherein the substitution of the first halogen of the cyanuric halide is done at a temperature in the range of 0 to 20° C., and at a pH in the range of 2 to 7, the substitution of the second halogen of the cyanuric halide is done at a temperature in the range of 20 to 60° C., and at pH in the range of 4 to 8, and substitution of the third halogen of the cyanuric halide is done at a temperature in the range of 60 to 102° C., and at a pH in the range of 7 to 10.

19. The sizing composition according to claim 1, wherein the protective polymer (d) comprises a polyethylene glycol (i).

20. The sizing composition according to claim 1, wherein the protective polymer (d) comprises (iv), (v), or (vi).

* * * * *